United States Patent [19]

Miller

[11] Patent Number: 4,511,746

[45] Date of Patent: * Apr. 16, 1985

[54] LOW ACTIVITY CATALYST OLIGOMERIZATION PROCESS

[75] Inventor: Stephen J. Miller, San Francisco, Calif.

[73] Assignee: Chevron Research Company, San Francisco, Calif.

[*] Notice: The portion of the term of this patent subsequent to Nov. 22, 2000 has been disclaimed.

[21] Appl. No.: 305,803

[22] Filed: Sep. 25, 1981

[51] Int. Cl.$^3$ .............................................. C07C 2/02
[52] U.S. Cl. .................................. 585/323; 585/510; 585/517; 585/530; 585/533
[58] Field of Search ............... 585/510, 530, 533, 531, 585/512, 322, 323

[56] References Cited

U.S. PATENT DOCUMENTS

| | | | |
|---|---|---|---|
| 3,325,465 | 6/1967 | Jones et al. | 260/94.9 |
| 3,756,942 | 9/1973 | Cattanach | 208/137 |
| 3,827,968 | 8/1974 | Givens et al. | 208/49 |
| 3,960,978 | 6/1976 | Givens | 260/683.15 |
| 4,211,640 | 7/1980 | Garwood et al. | 208/255 |
| 4,227,992 | 10/1980 | Garwood et al. | 208/46 |
| 4,247,728 | 1/1981 | Rubin et al. | 585/533 X |
| 4,254,295 | 3/1981 | Tabak | 585/533 |
| 4,289,607 | 9/1981 | Kokotailo | 585/533 X |
| 4,417,088 | 11/1983 | Miller | 585/533 |
| 4,423,269 | 12/1983 | Miller | 585/533 |

FOREIGN PATENT DOCUMENTS 1930001  1/1973  Fed. Rep. of Germany ...... 585/510

Primary Examiner—Delbert E. Gantz
Assistant Examiner—A. Pal
Attorney, Agent, or Firm—S. R. La Paglia; W. L. Stumpf; V. J. Cavalieri

[57] ABSTRACT

A process for the pure oligomerization of $C_2$–$C_6$ alkenes over low hydrogen transfer activity molecular sieves is disclosed.

7 Claims, 1 Drawing Figure

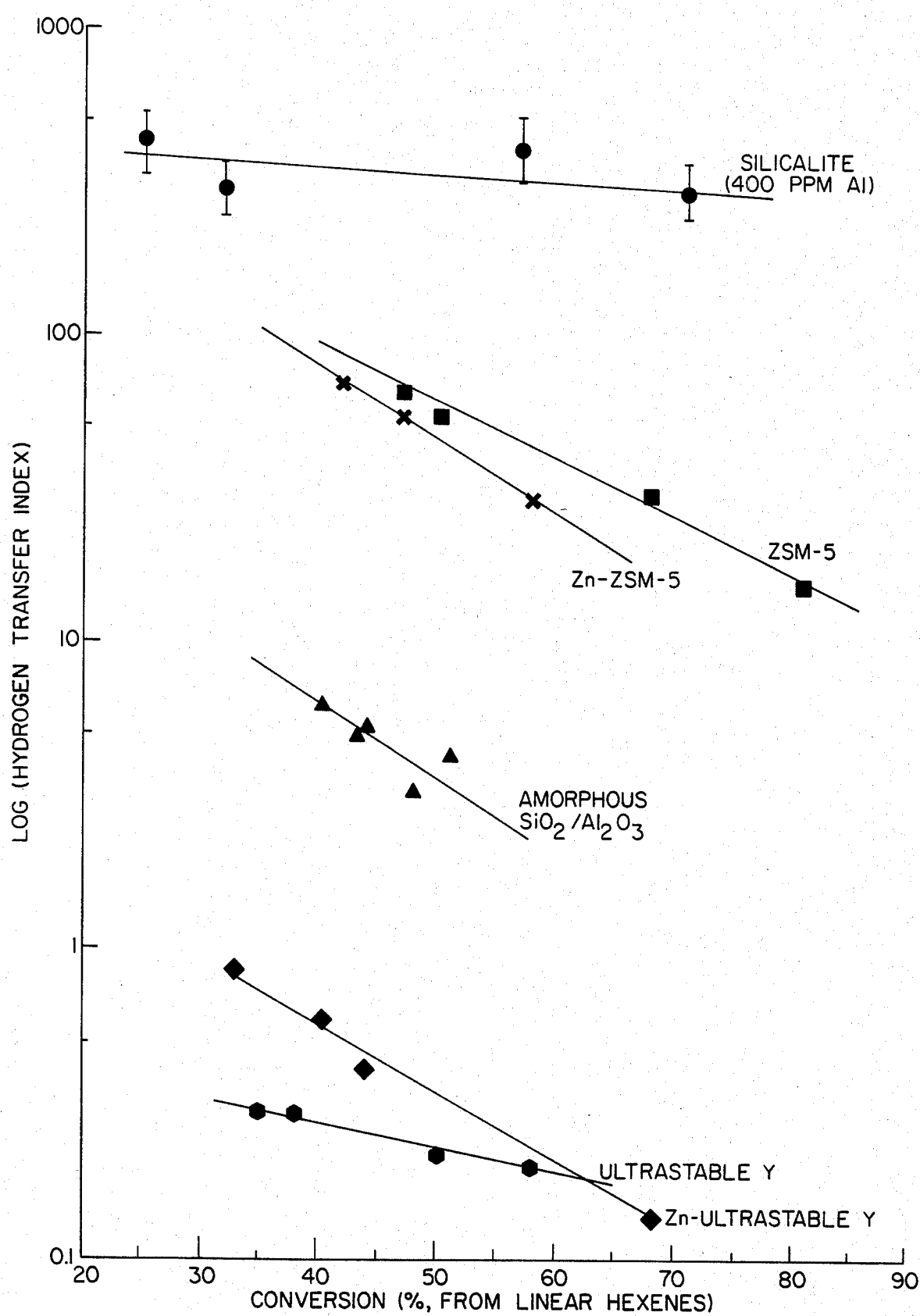

LOW ACTIVITY CATALYST OLIGOMERIZATION PROCESS

TECHNICAL FIELD

Among the most useful chemicals of modern society are the surfactants used in detergents. Detersive surfactants are of three general types, anionic, cationic, and nonionic. But one feature common to many surfactants is an alkyl side chain containing from about 8 to 12 carbon atoms. Nonionic ethoxylated alkylbenzenes, for example, typically have the formula:

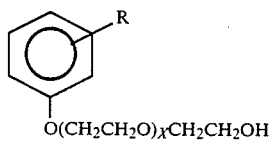

$O(CH_2CH_2O)_xCH_2CH_2OH$ in which X is 8-12 and R is a $C_{8-10}$ alkyl group. Anionic surfactants such as alkylbenzenesulfonates will typically have the formula:

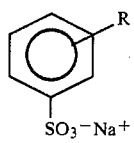

$SO_3^- Na^+$ wherein R is a $C_{10}-C_{14}$ alkyl group.

These alkylaromatic compounds can be synthesized by the alkylation of benzene or a benzene derivative with an alkene of the appropriate chain length. The usual alkene source is, ultimately, a $C_3$ to $C_6$ alkene. These lower alkenes are oligomerized to their multimers (e.g., dimer, trimer, tetramer). The multimer is then a reactant in the alkylation process.

Most oligomerization processes are typically catalytic and typically use multiphase systems. The standard oligomerization processes use phosphoric acid containing catalysts. Three major catalyst modifications involving phosphoric acid catalysts include (1) quartz wetted with liquid phosphoric acid, (2) solid pellets (e.g., Kieselguhr) impregnated with phosphoric acid and used in chambers, and (3) solid catalyst pellets impregnated with phosphoric acid and used packed in tubes surrounded by cooling water. Additionally, copper pyrophosphate has been used as a catalyst. These processes are used to convert olefinic gases, propenes and butenes, to gasoline range materials or petrochemical polymers.

A number of patents have issued relating to the preparation of aromatics from short chain olefins using highly active zeolites such as ZSM-5 (e.g., U.S. Pat. Nos. 3,756,942, Cattanach, Sept. 4, 1973; 3,827,968, Givens et al., Aug. 6, 1974; 3,960,978, Givens et al., June 1, 1976). Additionally, several patents disclose the preparation of gasoline and fuel oil range materials from short chain olefins such as propene and ethene (e.g., U.S. Pat. Nos. 4,227,992, Garwood et al., Oct. 14, 1980; 4,211,640, Garwood et al., July 8, 1980).

Even with the existence of phosphoric acid processes for making gasoline and petrochemical olefins and zeolitic processes for making gasoline, it can be appreciated that there is a continuing search for more efficient methods of preparing multimers of $C_3-C_6$ olefins which do not require solvent recovery steps or the use of liquid solutions, and yet which produce significant amounts of the multimers without cracking the product and producing other carbon chain length materials.

I have discovered that under certain reaction conditions and over certain very low activity catalysts, lower alkenes can be oligomerized to products which contain substantial amounts of their multimers.

These catalysts are very low alumina content intermediate pore size molecular sieves which, surprisingly, have catalytic activity. Additionally, they can catalyze "pure" oligomerization reactions which produce multimers of the feed alkene as opposed to the relatively unselective cracking/oligomerization reactions which take place over zeolites and silicates which contain higher amounts of aluminum. Surprisingly, deactivated intermediate pore size zeolites, such as those which have been deactivated by steam or coke, can also oligomerize lower alkenes to their multimers. Because the oligomerizations are selective, commercially useful oligomer compositions for use, in detergents for example, are prepared. Yet, these synthetic reactions do not require the solvent systems or replenishment of catalyst of standard synthetic processes. Further, the catalyst can be rejuvenated easily by simple stripping operations to achieve long run periods. Long run lives are also obtained by the use of high pressure operation.

TECHNICAL DISCLOSURE

My discoveries are embodied in an alkene oligomerization process, comprising:

(a) contacting a feed comprising $C_2$ to $C_6$ alkenes with a catalyst comprising an essentially alumina-free intermediate pore size silicaceous molecular sieve under oligomerization conditions; and (b) recovering an effluent comprising substantial amounts of multimers of said alkenes.

My discoveries are also embodied in an alkene oligomerization process, comprising:

(a) contacting a feed comprising $C_2$ to $C_6$ alkenes with a catalyst comprising an intermediate pore size zeolite, pretreated to have a very low hydrogen transfer activity, under oligomerization conditions; and (b) recovering an effluent comprising substantial amounts of multimers of said alkenes.

The feeds of the present process contain $C_2-C_6$ alkenes. Of course, where it is desired to produce a single specific multimer, a feed comprising a single alkene will be chosen. For example, to prepare a $C_9$ multimer, propene will be the preferred feed, while to produce a $C_{12}$ multimer, a butene or hexene will be the preferred feed. The preferred lower alkenes have from 3 to 6 carbon atoms and preferably have 3 or 4 carbon atoms.

By "multimers," as used herein, is meant the two to five unit oligomers prepared from an alkene; that is, the dimer, trimer, tetramer, and pentamer. The multimer most easily and desirably prepared using my process is the trimer. The oligomerization reaction zone conditions will typically include hydrocarbon partial pressures and temperatures such that at least some of the multimers produced are liquids in the reaction zone. Under these conditions, the reaction is surprisingly efficient for commercial operation in that catalyst fouling is greatly lowered and run lengths are greatly increased.

The reaction conditions of temperature and hydrocarbon partial pressure which will provide a liquid multimer phase can be easily determined using critical temperatures and pressures. Critical temperatures and pressures for pure organic compounds can be found in standard reference works such as *CRC Handbook of Chemistry and Physics, International Critical Tables, Handbook of Tables for Applied Engineering Science,* and Kudchaker, Alani, and Zwolinski, Chemical Reviews, 68, 659 (1968), all of which are incorporated herein by reference. The critical temperature for a pure compound is that temperature above which the compound cannot be liquefied, regardless of pressure. The critical pressure, is the vapor pressure of the compound at its critical temperature. These points for several pure alkenes are listed below:

|  | $T_c$ °C. | (F.°) | $P_c$-atm | (bar) |
|---|---|---|---|---|
| ethene | 9.21 | (48.6) | 49.66 | (50.3) |
| propene | 91.8 | (197.2) | 45.6 | (46.2) |
| 1-butene | 146.4 | (295.5) | 39.7 | (40.2) |
| 1-pentene | 191.59 | (376.9) | 40 | (40.5) |
| iso-2-pentene | 203 | (397) | 36 | (36.5) |
| 1-hexene | 230.83 | (447.49) | 30.8 | (31.2) |
| 1-heptene | 264.08 | (507.34) | 27.8 | (28.2) |
| 1-octene | 293.4 | (560.1) | 25.6 | (25.9) |
| 1-decene | 342 | (648) | 22.4 | (22.7) |

It can be appreciated that at temperatures above about 205° C. (401° F.), pure $C_5$ and lower alkenes must be gaseous, while pure $C_6$ and higher alkenes can still be liquefied by applying pressure. Similarly, above about 340° C. (644° F.) pure $C_{10}$ and higher alkenes can be maintained in the liquid state, while pure $C_9$ and lower alkenes must be gaseous.

Typical feeds and products are mixtures of compounds. But even so, once the chemical composition of the mixture is known, its critical temperature and pressure can be determined from the ratios of the chemicals and the critical points of the pure compounds. See for example, the methods of Kay and Edmister in *Perry's Chemical Engineers Handbook,* 4th Edition, pages 3-214, 3-215 (McGraw Hill, 1963), incorporated by reference.

The alkene chains can be branched. And, even though intermediate pore size molecular sieves are used, alkenes having quaternary carbons (two branches on the same carbon atom) can be used. But where quaternary carbons are present, it is highly preferred that the branches are methyl. It appears that even though the intermediate pore size molecular sieves do not admit quaternary carbon atoms into their pore structures, they have the capability of causing one of the quaternary substituents to migrate to a different position on the alkene chain, thereby forming two tertiary sites and an entity which can enter the intermediate sized pores.

The feed alkenes can be prepared from any source by standard methods. Sources of such lower alkenes can include FCC offgas, coker offgas, thermal cracking offgas, syngas (by use of CO reduction catalysts), low pressure, nonhydrogenative zeolite dewaxing, alkanols (using high silica zeolites), and dewaxing with crystalline silica polymorphs.

By "essentially alumina free intermediate pore size silicaceous molecular sieve," as used herein, is meant a silica containing crystalline material with a very low aluminum content.

These materials have the ability to sort molecules based on the size or the shape, or both of the molecules. The larger pore size materials will admit larger molecules than the smaller pore size materials. Intermediate pore size molecular sieves have the unique characteristic of being able to differentiate between large molecules and molecules containing quaternary carbon atoms on the one hand, and smaller molecules on the other.

By "intermediate pore size," as used herein, is meant an effective pore aperture in the range of about 5 to 6.5 Angstroms when the molecular sieve is in the H-form. Molecular sieves having pore apertures in this range tend to have unique molecular sieving characteristics. Unlike small pore zeolites such as erionite and chabazite, they will allow hydrocarbons having some branching into the molecular sieve void spaces. Unlike larger pore zeolites such as the faujasites and mordenites, they can differentiate between n-alkanes and slightly branched alkanes on the one hand and larger branched alkanes having, for example, quaternary carbon atoms.

The effective pore size of the molecular sieves can be measured using standard adsorption techniques and hydrocarbonaceous compounds of known minimum kinetic diameters. See Breck, *Zeolite Molecular Sieves,* 1974 (especially Chapter 8) and Anderson et al., J. Catalysis 58, 114 (1979), both of which are incorporated by reference.

Intermediate pore size molecular sieves in the H-form will typically admit molecules having kinetic diameters of 5.0 to 6.5 Angstroms with little hindrance. Examples of such compounds (and their kinetic diameters in Angstroms) are: n-hexane (4.3), 3-methylpentane (5.5), benzene (5.85), and toluene (5.8). Compounds having kinetic diameters of about 6 to 6.5 Angstroms can be admitted into the pores, depending on the particular sieve, but do not penetrate as quickly and in some cases are effectively excluded. Compounds having kinetic diameters in the range of 6 to 6.5 Angstroms include: cyclohexane (6.0), 2,3-dimethylbutane (6.1), 2,2-dimethylbutane (6.2), m-xylene (6.1), and 1,2,3,4-tetramethylbenzene (6.4). Generally, compounds having kinetic diameters of greater than about 6.5 Angstroms do not penetrate the pore apertures and thus are not absorbed into the interior of the molecular sieve lattice. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms. Among the materials falling within this range are the crystalline silica polymorph, silicalite, RE 29,948 organosilicates, and the chromia silicate, CZM.

In performing adsorption measurements to determine pore size, standard techniques are used. It is convenient to consider a particular molecule as excluded if it does not reach at least 95% of its equilibrium adsorption value on the zeolite in less than about 10 minutes (p/po=0.5; 25° C.).

By "crystalline silica polymorphs," as used herein, is meant materials having very low aluminum contents (or high silica:alumina mole ratios). Aluminum contents of these materials are generally less than about 1000 ppm, preferably less than about 750 ppm.

Intermediate pore size crystalline silica polymorphs useful in the present invention include silicalite, as disclosed in U.S. Pat. No. 4,061,724, and the "RE 29,948 organosilicates", disclosed in RE 29,948, both of which are incorporated by reference. The essentially alumina-free chromia silicate, CZM, is disclosed in Ser. No. 160,618, Miller, filed June 28, 1980, incorporated by reference.

Surprisingly, multimers of lower alkenes can also be prepared using intermediate pore size zeolites pretreated to have a very low hydrogen transfer activity.

Intermediate pore size zeolites include materials such as CZH-5 and members of the ZSM series, e.g., ZSM-5, ZSM-11, ZSM-12, ZSM-21, ZSM-23, ZSM-35, and ZSM-38. ZSM-5 is described in U.S. Pat. Nos. 3,702,886 and 3,770,614; ZSM-11 is described in U.S. Pat. No. 3,709,979; ZSM-12 is described in U.S. Pat. No. 3,832,449; ZSM-21 and ZSM-38 are described in U.S. Pat. No. 3,948,758; ZSM-23 is described in U.S. Pat. No. 4,076,842; ZSM-35 is described in U.S. Pat. No. 4,016,245; CZH-5 is disclosed in Ser. No. 166,863, Hickson, filed July 7, 1980. These patents and specifications are incorporated herein by reference. The intermediate pore size zeolites can include "crystalline admixtures" which are thought to be the result of faults occurring within the crystal or crystallite area during the synthesis of the zeolites. The "crystalline admixtures" are themselves zeolites but have characteristics in common, in a uniform or nonuniform manner, to what the literature reports as distinct zeolites. Examples of crystalline admixtures of ZSM-5 and ZSM-11 are disclosed and claimed in U.S. Pat. No. 4,229,424, Kokotailo, Oct. 21, 1980 (incorporated by reference). The crystalline admixtures are themselves intermediate pore size zeolites and are not to be confused with physical admixtures of zeolites in which distinct crystals or crystallites of different zeolites are physically present in the same catalyst composite or hydrothermal reaction mixture.

These zeolites are very active, so in order to produce substantial amounts of lower alkene multimers, they must be pretreated to lower their hydrogen transfer activity as well as their general catalytic activity. The usual pretreatments to reduce these activities are steaming or coking. A zeolite which is undesirably deactivated for many catalytic processes is surprisingly efficient at producing multimers as opposed to an undifferentiated product with mixtures of cracked and reassembled compounds. Therefore, a zeolite which has been used in other processes and which has been coked can be used to make multimers without being regenerated.

The intermediate pore size materials can be made even more active and stable for oligomerization by including the Group IIB metals, zinc or cadmium. A primary characteristic of these substituents is that they are weak bases, and are not easily reduced. These metals can be incorporated into the catalysts using standard impregnation, ion exchange, etc., techniques. Other metals such as calcium and the rare earths may be included in the catalyst. If hydrogen is not added to the feed, Group VIII metals (such as nickel, cobalt, palladium, and platinum) as well as other metals (such as vanadium, titanium, manganese, and rhenium) may be included in the catalyst. Mixtures of these metals may also be present. Strongly basic metals such as the alkali metals are unsatisfactory as they poison substantially all of the polymerization sites on the molecular sieve. For this reason, the alkali metal content of the molecular sieves is less than 1%, preferably less than 0.1%, and most preferably less than 0.01%. The most preferred substituents for use are zinc and cadmium, of these zinc is preferred. Zinc and cadmium are typically present on the catalyst in the range of about 0.01 to about 10 wt. %.

The use of zinc or zinc compounds as the substituent on the molecular sieves gives surprising stability, yields, and activity in the liquid olefin oligomerization processes described herein.

The oligomerization processes of the present invention are surprisingly more efficient with small crystallite sieve particles than with larger crystallite particles. Preferably, the molecular sieve crystals or crystallites are less than about 10 microns, more preferably less than about 1 micron, and most preferably less than about 0.1 micron in the largest dimension. Methods for making molecular sieve crystals in different physical size ranges are known to the art.

The molecular sieves can be composited with inorganic matrix materials, or they can be used with an organic binder. It is preferred to use an inorganic matrix since the molecular sieves, because of their large internal pore volumes, tend to be fragile, and to be subject to physical collapse and attrition during normal loading and unloading of the reaction zones as well as during the oligomerization processes. Where an inorganic matrix is used, it is highly preferred that the matrix be substantially free of hydrocarbon conversion activity.

The process is typically operated at a temperature less than about 350° C. and at pressures above 40 bar, preferably above 65 bar.

Once the effluent from the oligomerization reaction zone is recovered, a number of further processing steps involving the alkenes alone can be performed before further synthetic reactions take place.

All or part of the effluent can be contacted with the molecular sieve catalyst in further reaction zones to further react unreacted alkenes and alkene oligomers with themselves and each other to form still longer chain materials. Of course, the longer the carbon chain, the more susceptible the compound is to being cracked. Therefore, where successive oligomerization zones are used, each zone must be operated at conditions which do not cause cracking of the oligomers or multimers. It is most convenient to use reaction conditions in each reaction zone which are less severe than the reaction conditions in the immediately preceding zone. Operating with oligomerization zones in series with decreasing severity can also make process control of the exothermic oligomerization reactions much easier.

One particularly desirable method of operation is to separate unreacted alkenes present in the effluent from the alkene oligomers present in the effluent and then to recycle the unreacted alkenes back into the feed.

The run life of the catalyst in the oligomerization reaction zone can be greatly and surprisingly increased by periodically stopping the flow of feed into the reaction zone and stripping the catalyst with a stripping gas (such as hydrogen, nitrogen, or water vapor).

By "substantial amounts of multimer," as used herein, is meant a normally liquid product which contains greater than about 25% multimer, and preferably greater than about 50% multimer.

FIGURE

FIG. 1 illustrates the hydrogen transfer index of several alumina and silica containing materials.

EXAMPLE 1

A series of experiments was performed to examine the hydrogen transfer activity of molecular sieves. A feed pulse of fixed volume (0.5 microliter) from a heated Valco valve was carried into a small, fixed catalyst bed located in a stainless steel reactor. The reaction was entirely gas phase and isothermal. The hydrocarbon feed pulse was carried to the catalyst bed by a known velocity nitrogen stream at a high linear rate. The nitrogen stream was passed through a 4A/5A molecular sieve purifier before contacting the feed. The catalyst bed contained −250 mesh catalyst fines which, depending on the catalyst, were diluted with the same size mesh alumina. The diluent alumina was added as needed to reduce the catalyst activity so all catalysts could be measured at roughly identical feed conversions. The catalyst was finally diluted (4:1) with 80–100 mesh, acid washed Alundum to improve catalyst dispersion and to help maintain a true isothermal bed temperature. Reactor pressure was controlled by an Annin valve.

The entire gas stream, containing the reacted feed pulse, was taken directly through heated lines to the injector splitter of a capillary gas chromatograph equipped with a flame ionization detector.

The reaction conditions include a catalyst temperature of 221° C. (430° F.), total pressure of 34.5 bar (500 psi) and a nitrogen carrier gas flow of 800 cc/min. at STP. The injection volume was 0.5 microliter. Hydrocarbon analysis was performed using a 50-meter OV-101 fused silica capillary column. The catalyst was continually exposed to the nitrogen carrier gas between injections.

The hydrogen transfer index calculated from the test results is the ratio of 3-methylpentenes to 3-methylpentane produced from a 1-hexene feed, with a linear hexene conversion from 30% to 70%.

The contact time was computed from the temperatures and pressure corrected linear velocity of the nitrogen carrier stream and the length and volume of the catalyst bed. The computed WHSV and catalyst/oil ratio were based solely on the active component content within the bed.

The catalysts tested are listed in Table 1.

TABLE 1

| Catalyst | | $SiO_2/Al_2O_3$ Mole Ratio |
|---|---|---|
| (A) | ZSM-5 | 78:1 |
| (B) | Silicalite | 230:1 |
| (C) | Silicalite | 2200:1 |
| (D) | Ultrastable Y | 6:1 |
| (E) | Dealuminated Mordenite | 63:1 |
| (F) | Amorphous $SiO_2/Al_2O_3$ | 54/46 (wt. ratio) |
| (G) | CZH-5 | 50:1 |

The results obtained are listed in Table 2. Experiments with Catalysts (A) and (B) were performed after impregnating the catalysts with 0.8 weight percent zinc.

TABLE 2

| Catalyst | 20% A 80% $Al_2O_3$ | 20% A 80% $Al_2O_3$ | 65% B | 65% C | 12% D 88% $Al_2O_3$ | 18% E 82% $Al_2O_3$ | 100% F | 100% G |
|---|---|---|---|---|---|---|---|---|
| Inj. Number | 3 | 3 | 3 | 2 | 3 | 1 | 2 | 1 |
| Catalyst Wt (mg Sieve) | 4.4 | 4.1 | 19 | 24 | 2.8 | 4.2 | 35 | 19.3 |
| Zn (0.8%): Yes/No | No | Yes | Yes | No | No | No | No | No |
| Alundum Dilution | 4:1 | 4:1 | 4:1 | 3:1 | 4:1 | 4:1 | 4:1 | 4:1 |
| Contact Time (sec) | 0.25 | 0.36 | 0.33 | 0.41 | 0.28 | 0.23 | 0.34 | 0.4 |
| WHSV (1/hr) | 1100 | 806 | 200 | 120 | 1500 | 1220 | 100 | 157 |
| Cat/Oil | 13 | 12 | 57 | 71 | 9 | 13 | 104 | 57 |
| Conversion From Linear Hexenes (%) | 47 | 42 | 41 | 56 | 38 | 48 | 43 | 53 |
| $K_{Hexenes}$ (1/sec) | 2.54 | 1.51 | 1.60 | 2.00 | 1.71 | 2.84 | 1.65 | 1.88 |
| Product Yield, Wt % | | | | | | | | |
| $C_4$ Minus | 13 | 12.6 | 14 | 13.3 | 3.5 | 17.1 | 0.3 | 12 |
| $C_5$ | 11 | 10 | 8.4 | 8.5 | 4.2 | 12.9 | 3 | 8 |
| $C_6$ | 57 | 58.8 | 62 | 53.6 | 63.2 | 55.7 | 76.4 | 73 |
| $C_7$ | 4 | 4.2 | 4.1 | 5.5 | 4.7 | 4.4 | 3.5 | 2 |
| $C_8$ | 7.5 | 5.6 | 5.4 | 7.9 | 5.9 | 5.2 | 4.1 | 3.7 |
| $C_9$ | 4 | 3.6 | 2.5 | 4.3 | 4.3 | 2.4 | 2.4 | 1.3 |
| $C_{10}+$ | 1.9 | 2.8 | 2.3 | 4.9 | 10.7 | 1.1 | 10.1 | 0.3 |
| Hydrogen Transfer Index | | | | | | | | |
| 3M-Pentenes/ 3M-Pentane | 66 | 70 | 105 | 500 | 0.30 | 1.0 | 5 | 6 |

The graph of FIG. 1 illustrates the differences in hydrogen transfer index for several catalysts, as well as the response of the hydrogen transfer index to the number of hexene injections, i.e., to the fouling of the catalyst.

The lower the hydrogen transfer activity of the catalyst, the higher the hydrogen transfer index. By "very low hydrogen transfer activity" is meant a hydrogen transfer index greater than about 100, preferably greater than about 200.

EXAMPLE 2

An experiment was performed to prepare propene multimers over a silicalite (400 ppm Al) catalyst which also contained 1 wt. % zinc. The pressure was 110 bar (16000 psig), the LHSV was 0.5. After 5 hours operation at 288° C. (550° F.), the product was 14%, C, 26% $C_9$, and 6.4% above $C_{17}$. At 6 hours onstream, the temperature was raised to 316° C. (600° F.). After 46 hours onstream, the product was 19% $C_6$, 41% $C_9$, and a total of 29% above $C_9$ (18% $C_{12}$; 21% above $C_{17}$). After 54 hours onstream, the temperature was lowered to 288° C. (550° F.) and the product was 21% $C_6$ and 65% $C_9$.

This experiment shows that significant amounts of multimers can be obtained from an alkene feed. Similar results can be obtained with the other lower alkenes, and especially with the $C_4$ alkenes, as well as with intermediate pore-size zeolites which have been pretreated to have a very low hydrogen transfer activity.

I claim:

1. An alkene oligomerization process comprising:
   (a) contacting a $C_2$ to $C_6$ alkene with an essentially alumina-free molecular sieve selected from the group consisting of silicalite, RE 29,948 organosilicate, or CZM at a temperature of less than 350° C. and a pressure greater than about 40 bar; and
   (b) recovering an effluent comprising substantial amounts of olefin multimers containing from 2 to 5 units of said alkene.

2. The process of claim 1 wherein at least some of said multimers are liquids under said oligomerization conditions.

3. The process of claim 1 wherein said oligomerization conditions include a pressure greater than about 65 bar.

4. The process of claim 1, further comprising the steps of:
   separating unreacted alkenes present in said effluent from said alkene multimers; and
   recycling said unreacted alkenes into said feed.

5. The process of claim 1, further comprising the step of:
   alkylating an aromatic compound with at least part of said multimers under alkylation conditions.

6. The process of claim 5 wherein said aromatic compound is benzene.

7. The process of claim 1, wherein said catalyst further comprises zinc or a compound thereoff, cadmium or a compound thereoff, or mixtures thereoff.

* * * * *

UNITED STATES PATENT AND TRADEMARK OFFICE
CERTIFICATE OF CORRECTION

PATENT NO. : 4,511,746
DATED : April 16, 1985
INVENTOR(S) : Stephen J. Miller

It is certified that error appears in the above-identified patent and that said Letters Patent are hereby corrected as shown below:

Col. 8, line 54, "(16000 psig)" should read --(1600 psig)--

Col. 8, line 55, "14%, C," should read --14% $C_6$--

Signed and Sealed this

Twenty-ninth Day of October 1985

[SEAL]

Attest:

DONALD J. QUIGG

Attesting Officer

Commissioner of Patents and Trademarks—Designate